(12) United States Patent
Reu et al.

(10) Patent No.: US 6,755,822 B2
(45) Date of Patent: Jun. 29, 2004

(54) DEVICE AND METHOD FOR THE CREATION OF A CIRCUMFERENTIAL CRYOGENIC LESION IN A PULMONARY VEIN

(75) Inventors: Eugene Brian Reu, San Diego, CA (US); Thomas M. Castellano, Temecula, CA (US); Gregory M. Ayers, Los Altos, CA (US)

(73) Assignee: CryoCor, Inc., San Diego, CA (US)

( * ) Notice: Subject to any disclaimer, the term of this patent is extended or adjusted under 35 U.S.C. 154(b) by 0 days.

(21) Appl. No.: 09/872,117

(22) Filed: Jun. 1, 2001

(65) Prior Publication Data

US 2002/0183730 A1 Dec. 5, 2002

(51) Int. Cl.⁷ ............................................. A61B 18/18
(52) U.S. Cl. .......................... 606/21; 607/122; 606/41
(58) Field of Search ............................... 606/21–26, 41, 606/46, 47; 607/101–102, 122

(56) References Cited

U.S. PATENT DOCUMENTS

| | | | |
|---|---|---|---|
| 4,569,801 A | 2/1986 | Molloy et al. | |
| 4,641,649 A | 2/1987 | Walinsky et al. | |
| 4,673,563 A | 6/1987 | Berne et al. | |
| 4,898,591 A | 2/1990 | Jang et al. | |
| 5,487,385 A | 1/1996 | Avitall | |
| 5,582,609 A | 12/1996 | Swanson et al. | |
| 5,617,854 A | 4/1997 | Munsif | |
| 5,733,280 A | * 3/1998 | Avitall | 606/23 |
| 6,012,457 A | 1/2000 | Lesh | |
| 6,235,025 B1 | * 5/2001 | Swartz et al. | 606/45 |
| 6,325,797 B1 | * 12/2001 | Stewart et al. | 606/41 |
| 6,330,473 B1 | * 12/2001 | Swanson et al. | 607/122 |

FOREIGN PATENT DOCUMENTS

| | | |
|---|---|---|
| FR | 2 447 406 | 9/1981 |
| FR | 2 482 445 | 11/1981 |

OTHER PUBLICATIONS

W. Haverkame et al., "Non–pharmacological treatment of arrhythmla using the method of trans–catheter ablation", Grud Serdechnososudistaia Khir, Aug. 1991, pp. 6–16, vol. 8, [ABSTRACT].

Haissaguerre et al., "Right and Left Atrial Radiofrequency Catheter Therapy of Paroxysmal Atrial Fibrillation", Journal of Cardiovascular Electrophysiology, vol. 7, No. 12, Dec. 1996, pp. 1132–1144.

Cox et al., "The surgical treatment of atrial fibrillation", The Journal of Thoracic and Cardiovascular Surgery, vol. 101, No. 3, Mar. 1991, pp. 402–405.

* cited by examiner

*Primary Examiner*—Michael Peffley
(74) *Attorney, Agent, or Firm*—Fay Kaplun & Marcin, LLP (57) ABSTRACT

A device and method for ablating tissue includes a sheath system with an occlusion structure. In certain embodiments, arrhythmias originating in pulmonary veins are treated cryogenically.

27 Claims, 8 Drawing Sheets

DEVICE AND METHOD FOR THE CREATION OF A CIRCUMFERENTIAL CRYOGENIC LESION IN A PULMONARY VEIN

INCORPORATION BY REFERENCE

The entire disclosures of each of U.S. Pat. No. 6,035,657, issued Mar. 14, 2000 for a FLEXIBLE CATHETER CRYOSURGICAL SYSTEM ("the '657 patent"), U.S. Pat. No. 5,910,104 issued Jun. 8, 1999 for a CRYOSURGICAL PROBE WITH DISPOSABLE SHEATH ("the '104 patent") and U.S. Pat. No. 5,275,595 issued Jan. 4, 1994 for a CRYOSURGICAL INSTRUMENT ("the 595 patent"), all assigned to CryoGen, Inc. of San Diego, Calif. are hereby expressly incorporated by reference in their entireties.

FIELD OF THE INVENTION

The present invention relates generally to devices and methods for the treatment of cardiac arrhythmia and more specifically relates to devices and methods for the treatment of focal atrial arrhythmia.

BACKGROUND INFORMATION

Cardiac rhythm is maintained by precisely timed nerve signals electrically exciting and being conducted through cardiac tissue to stimulate synchronous contractions of the four heart chambers (2 ventricles and 2 atria). In a normal sinus rhythm, the nerve signals are typically conducted along paths initiating at the sino-atrial (SA) node and passing from there through the atrioventricular (AV) node and the bundle of His to the ventricular myocardial tissue.

Potentially dangerous abnormal cardiac rhythms, or arrhythmias, including atrial fibrillation, are common medical conditions which may result from disturbances in the site of origin and/or the pathways of conduction of the nerve signals exciting contraction of the four chambers of the heart. The site of origin and pathways of conduction of these signals are currently mapped, for example using an electrocardiograph (ECG) in conjunction with mapping methods such as those described in U.S. Pat. No. 4,641,649 to Walinsky et al.

One common type of atrial fibrillation occurs when the contraction initiating signals originate within one or more of the pulmonary veins rather than at the SA node. These atrial arrhythmias have been treated by a variety of methods including pharmocologic treatments, highly invasive surgical procedures and linear and circumferential RF ablations of the myocardial wall. However, each of these methods has drawbacks, e.g., the pain and extended recovery time for invasive surgery, relative ineffectiveness of pharmacologic treatments and restenosis at the ablation site due to the application of RF energy or other heat based therapies thereto.

SUMMARY OF THE INVENTION

The present invention is directed to a method and apparatus for ablating tissue within a patient comprising inserting into a patient's venous system a substantially rigid sheath, piercing a desired point of penetration in the patient's interatrial septum to pass the rigid sheath through the interatrial septum into the patient's left atrium, maneuvering a flexible section mounted on the rigid sheath into a position in which a distal end of the flexible section is located adjacent to a portion of tissue to be ablated, the flexible section including an occluding structure which has a retracted position and extended position, and passing an ablation catheter through the flexible section so that an ablation tip of the ablation catheter is adjacent to the portion of tissue to be ablated.

DETAILED DESCRIPTION

The present invention may be further understood with reference to the following description and the appended drawings, wherein like elements are provided with the same reference numerals.

When arrhythmia resulting from the origination of contraction initiating signals within one or more of the pulmonary veins rather than at the SA node is detected, known techniques may be used to locate the point of origination and the path of conduction. After this data has been obtained, the device and method according to the present invention allows a user to ablate a portion of the identified pulmonary vein near the orifice or collar of the pulmonary vein to create a circumferential conduction block preventing these improper contraction origination signals from propagating into the left atrium and restoring a normal sequence of contractions.

Figure 1:
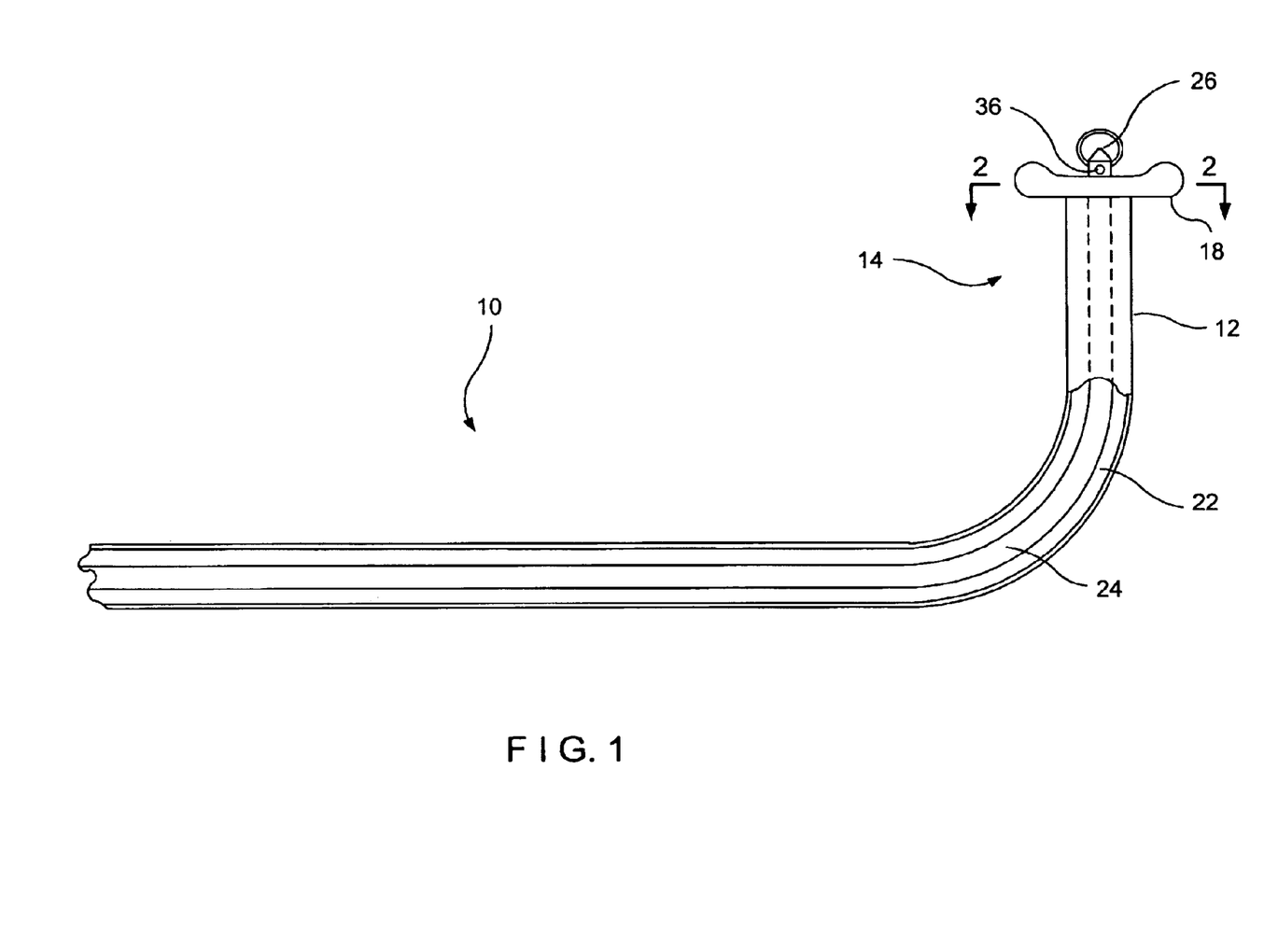
FIG. 1 shows a partially cross-sectional side view of a device according to the present invention.
Figure 2:
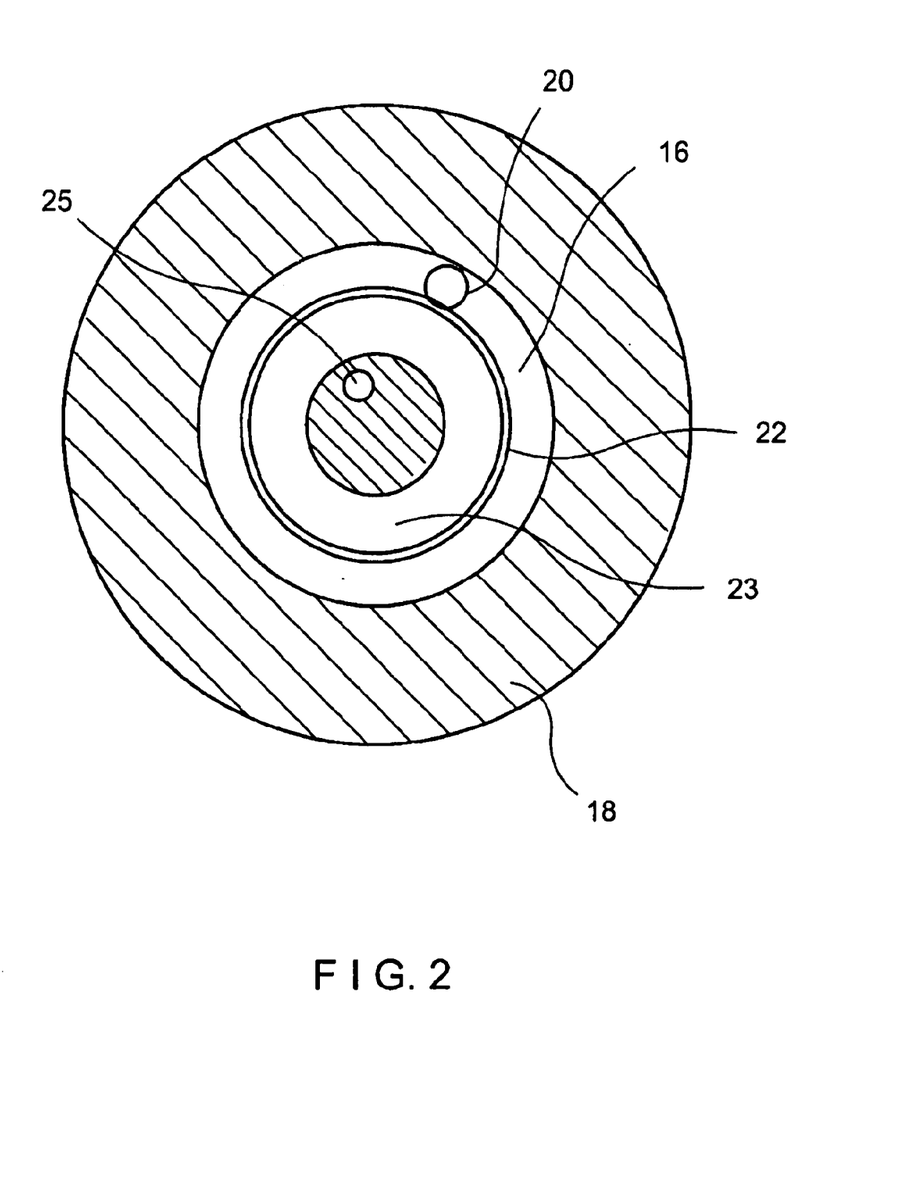
FIG. 2 shows a cross-sectional view of the device of FIG. 1, taken along line 2—2.

As shown in FIG. 1, the device 10 may include a flexible section 12 which is flexible laterally but is axially stiff so that it may be pushed distally to seal the orifice as will be described below. The flexible section 12 according to this embodiment of the invention may be formed as a sheath extending from a proximal end (not shown) which remains outside a patient's body to a distal end 14 which, when the device 10 is in an operative position is located within the patient's body. As shown in FIG. 2, the flexible section 12 includes a central lumen 16 extending therethrough from the proximal end to the distal end 14. As shown in FIGS. 1 and 2, an annular balloon 18 is mounted to the flexible section 12 adjacent to the distal end 14 and is coupled to an inflation lumen 20 extending along the outside of the flexible section 12 from the proximal end to the distal end 14 at which the inflation lumen 20 is fluidly coupled to the balloon 18. Alternatively, inflation lumen 20 may extend internally along the device. A rigid sheath 22 is slidably received within the flexible section 12. Alternatively, the flexible section 12 may simply consist of a flexible sheath 12' extending from a distal end of the rigid sheath 22 as described below in regard to FIG. 10.

The rigid sheath 22 may have a predetermined shape selected to aid in the insertion of the device 10 into the left atrium (LA) via a transeptal puncture and an approach from the inferior vena cava into the right atrium (RA) as will be described in more detail below. Specifically, the rigid sheath 22 may preferably have an outer diameter of between 9 and 14 French, more preferably approximately 11 French. Those skilled in the art will understand that an outer diameter of the flexible section 12 will be slightly larger than that of the rigid sheath 22, while the ablation catheter 24 will have an outer diameter slightly smaller than that of the rigid sheath 22. For example, an ablation catheter 24 with an outer diameter of 10 French may be slidably received within a rigid sheath 22 having an outer diameter of 11 French with an flexible section 12 having an 11.5 French outer diameter.

An ablation catheter 24 is slidably received within a central lumen of the rigid sheath 22 so that the ablation catheter 24 may be advanced distally beyond a distal end of the rigid sheath 22 to an extended position in which a cryogenic tip 26 mounted at a distal end of the ablation catheter 24 extends distally beyond a distal end of the flexible section 12. The ablation catheter 24 and the cryogenic tip 26 may, for example, be constructed in accord with the teaching of any of the '657, 104 and '595 patents. Specifically, the ablation catheter 24 may include a high pressure refrigerant lumen 25 extending through the ablation catheter 24 to a Joule-Thomson expansion element, e.g., a capillary tube, which opens into an expansion chamber formed within the cryogenic tip 26. Furthermore, the ablation catheter 26 may include one or more electrodes as described in the '657 patent which may be used to locate and map the site of the origin of the improper contraction origination signals.

In one embodiment, the catheter 24 may be a cryosurgical catheter that uses a two stage Joule-Thompson cooling system. A first loop, which may be closed or open, may extend into the tip of catheter 24. This first open loop may be pre-cooled by a second loop, which may be closed or open, whereby at least the high pressure portion of the first loop and the low pressure portion of the second loop are placed in a heat exchange relationship. In certain embodiments, the fluid circulating in the first loop may be a mixed gas refrigerant. The mixed gas refrigerant may include a hydrocarbon. As another example, the refrigerant in the first loop may be nitrous oxide.

Furthermore, in certain embodiments of the invention, the catheter 24 may be deflectable. That is, the catheter tip may be deflectable via a deflection mechanism associated with the catheter handle. In use, the deflectable section of the catheter will be generally within or extending from the flexible section 12. This combination of the deflectable catheter and flexible section may allow the device 10 to more easily be positioned in the desired pulmonary vein, as explained below.

When a user (e.g., an electro-physiologist or EP) has previously determined that contraction origination signals are improperly originating from a site within one of the pulmonary veins (PV), using, for example, electro-physiology (EP study) the device 10 is inserted into the LA of the patient using the Seldinger technique as is known to those skilled in the art as follows. Of course, those skilled in the art will understand that, where an EP study has not previously been performed, an EP mapping catheter may be inserted into the LA via the rigid sheath 22 of the device 10.

Figure 3:
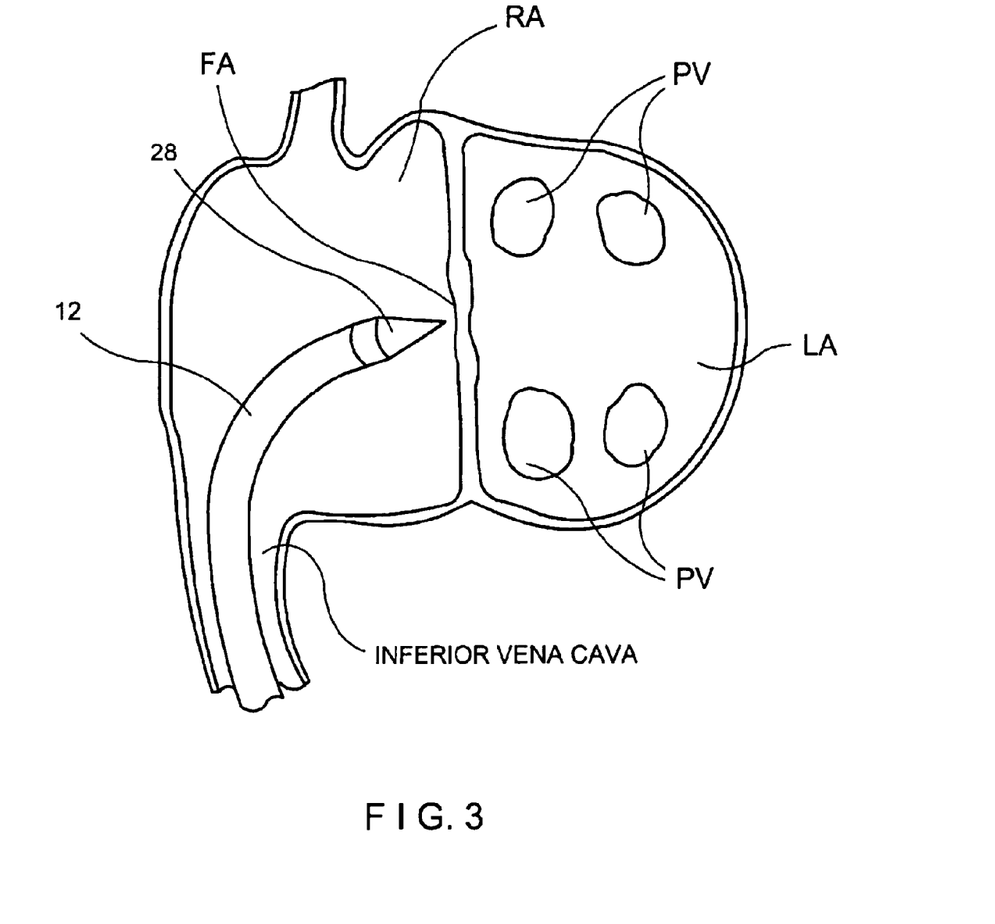
FIG. 3 shows a view of the device in position within the right atrium of a patient with a distal tip of a dilator adjacent to the foramen ovale.

Specifically, a guide wire (not shown) is inserted into the RA through the inferior vena cava. The rigid sheath 22 is inserted into the flexible section 12 and is then advanced along the guide wire until a distal end of the rigid sheath enters the RA via the inferior vena cava, as shown in FIG. 3. Further advancing the rigid sheath 22 and the flexible section 12 distally along the guide wire will advance the bent section of the rigid sheath 22 toward the point at which the inferior vena cava enters the RA. The bend in the rigid sheath 22 is selected so that, at this point, a distal end of the rigid sheath 22 is pointed substantially toward a position on the interatrial septum at which the foramen ovale (FO) is located. The dimensions of the rigid sheath 22 are also selected so that, at this point, the distal end of the rigid sheath 22 is positioned adjacent to the FO. The curvature of the rigid sheath 22 may preferably be between 30 and 90 degrees depending on the anatomy of the patient, and in one embodiment a 60 degree curvature is used.

Figure 4:
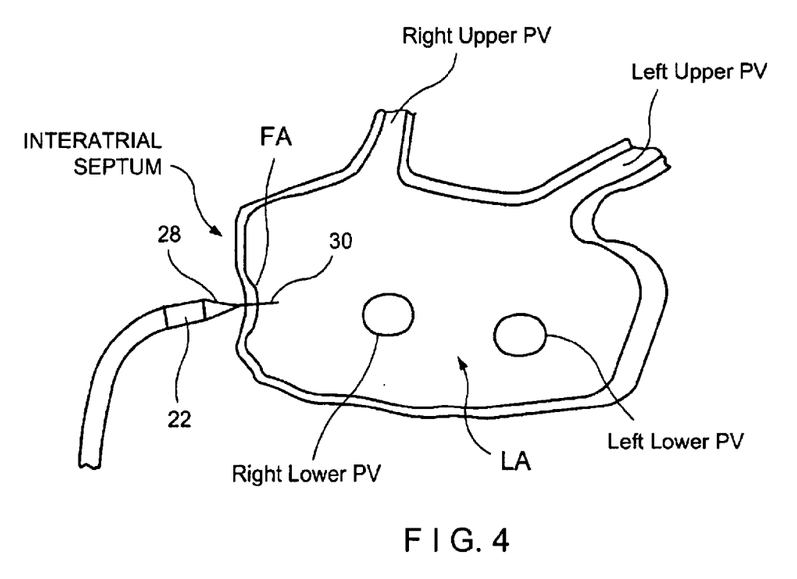
FIG. 4 shows a side view of the device of FIG. 1 in position with a needle penetrating the foramen ovale of a patient.
Figure 5:
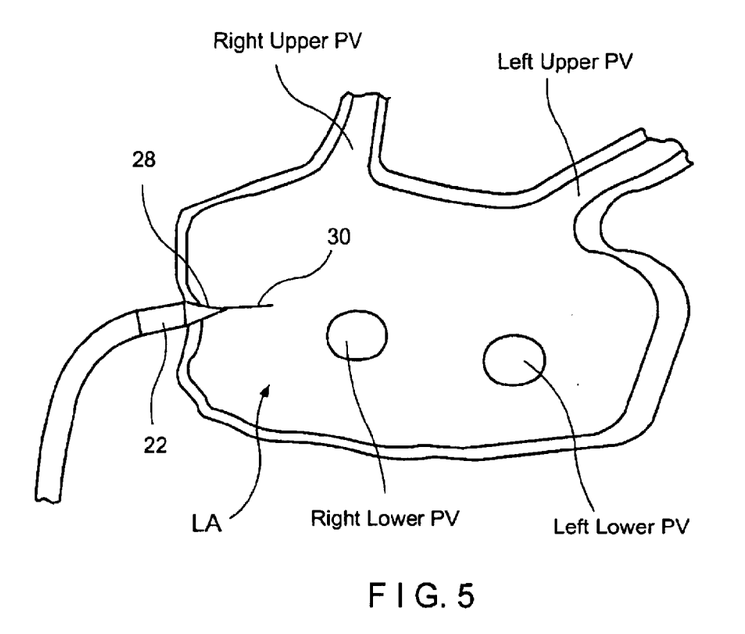
FIG. 5 shows a side view of the device of FIG. 1 in position with a dilator penetrating the opening in the foramen ovale made by the needle of FIG. 4.

As shown in FIGS. 3 and 4, a dilator 28 with a Brouchenborogh needle 30 received therein is then inserted through a central lumen 23 of the rigid sheath 22 until a distal end of the dilator 28 extends beyond a distal end of the rigid sheath 22. The user may then probe the interartial septum noting the relative strength of various locations on the interatrial septum until the precise location of the FO is determined (i.e., the FO forms a soft apical spot on the septum). Those skilled in the art will understand that intracardiac ultrasound may also be used to assist in locating the FO. Then the Brouchenborogh needle 30 is extended from the distal end of the dilator 28 to pierce the FO forming a transeptal puncture (TP) extending into the LA as shown in FIG. 4. The dilator 28 is then advanced through the TP in the interatrial septum to expand a diameter of the TP as shown in FIG. 5.

Figure 6:
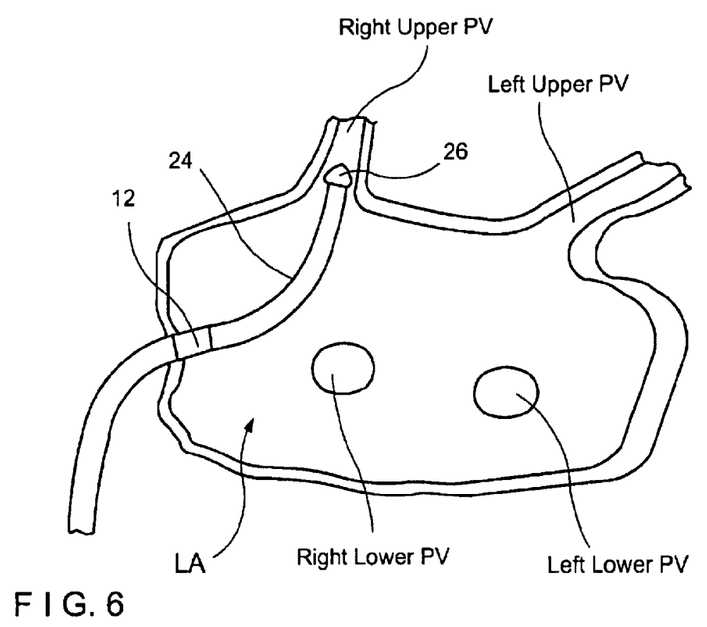
FIG. 6 shows a side view of the device of FIG. 1 in position within a pulmonary vein.

Thereafter, the Brouchenborogh needle 30 is retracted into the dilator 28 and removed from the body. The rigid sheath 22 is then advanced along the dilator 28 to pass through the TP into the LA. The flexible section 12 is then pushed along the rigid sheath 22 (utilizing the longitudinal rigidity of the flexible section 12) until a distal end of the flexible section 12 extends through the opening in the interatrial septum into the LA as shown in FIG. 6.

The ablation catheter 24 is then advanced distally through the rigid sheath 22 until the cryogenic tip 26 extends distally beyond the distal end of the rigid sheath 22 and the distal end of the flexible section 12. At this point there are several known techniques for maneuvering a catheter to a desired position within the opening of the one of the PV's from which the contraction origination signals are improperly originating. In certain embodiments, the catheter 24 is deflectable via a deflection mechanism associated with the catheter handle, which may ease the positioning of the catheter. Furthermore, by advancing the rigid sheath 22 further into the LA, the bend in the rigid sheath may be employed to assist in aiming the cryogenic tip 26 toward the desired PV opening. After the cryogenic tip 26 has been properly positioned well within the PV, the flexible section 12 is advanced distally along the ablation catheter 24 until the distal end of the flexible section is near the orifice at which the PV opens into the LA. To aid in ensuring proper positioning of the cryogenic tip 26 and the flexible section 12 in the orifice of the PV, the flexible section 12 and the rigid sheath 22 include radiopaque markers at the respective distal ends thereof or other desired locations.

Figure 7:
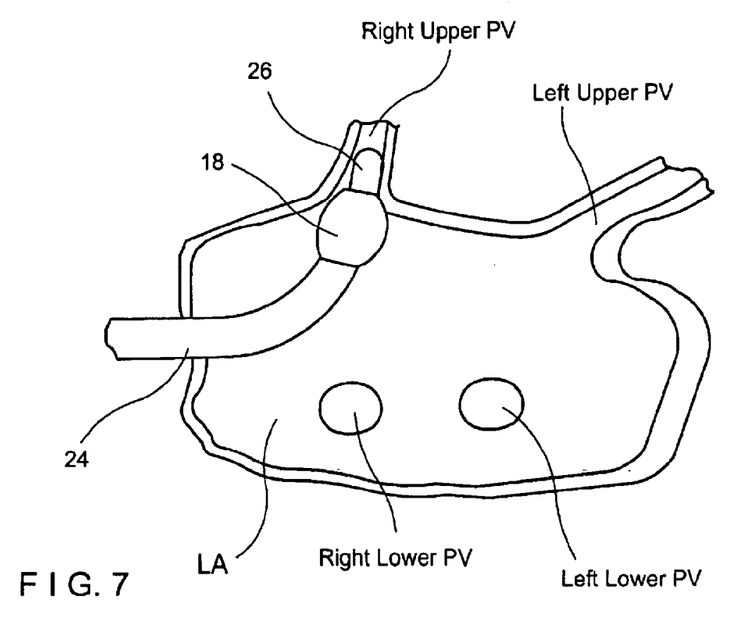
FIG. 7 shows a side view of the device of FIG. 1 in position within the pulmonary vein with an occluding balloon inflated.

Once the flexible section 12 has been positioned near the opening to the PV, the user may inject radiopaque dye into the PV via the flexible section 12 with the radiopaque fluid exiting the flexible section 12 via openings 36 located distally of the balloon 18. This may be done so as to aid in locating, under imaging, the orifice of the PV. The user may then inflate the balloon 18 by coupling a source of inflation fluid (not shown) to a proximal end of the inflation lumen 20. In one embodiment, the inflation fluid may be a diluted radiopaque or contrast fluid such that the balloon may more easily be seen under imaging. The flexible section 12 is then advanced until the balloon 18 is seated on the orifice of the PV, thereby occluding the flow of blood from the PV into the LA as shown in FIG. 7. The description herein of a balloon does not imply that blood flow must be occluded by an inflatable cuff. Rather, any structure which is radially extendible from the sheath 12 to occlude blood flow therepast will serve the purposes of this invention. There are many alternative constructions for this structure, which will be known to those skilled in the art.

Figure 8:
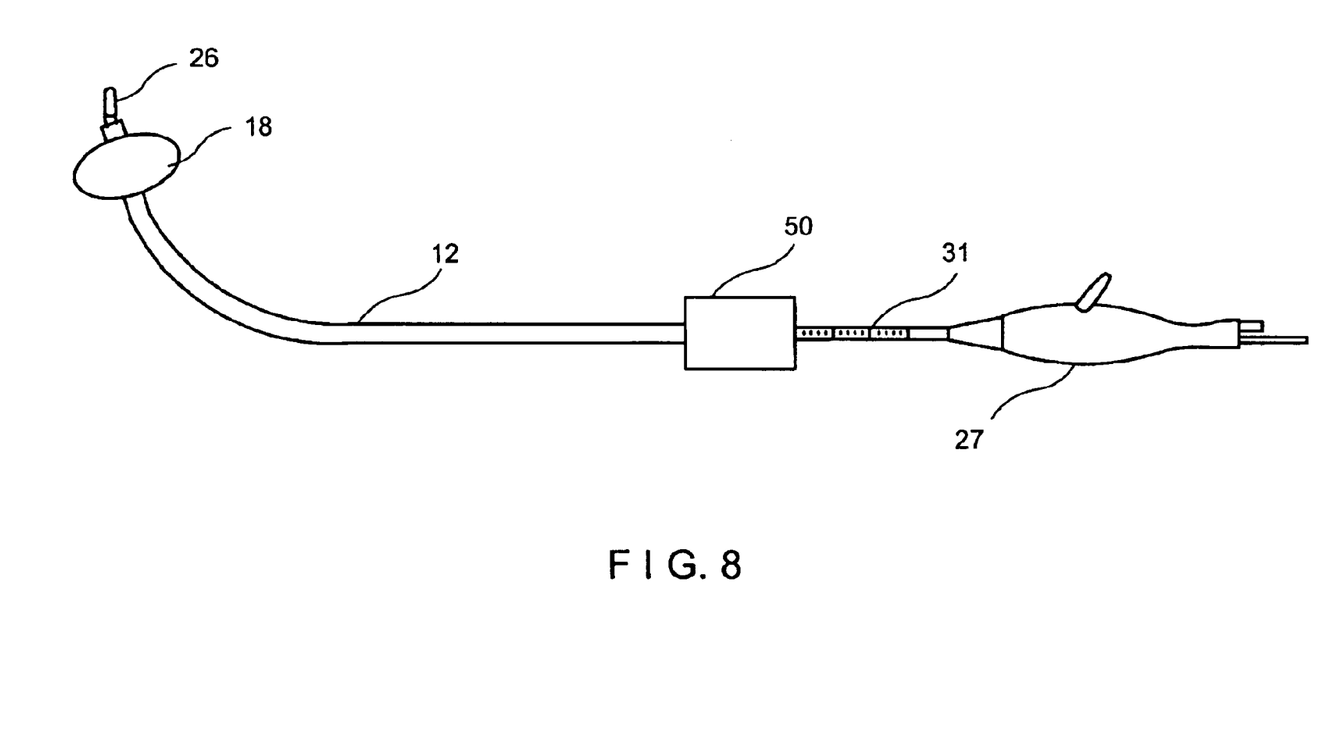
FIG. 8 shows the depth markers of the catheter according to certain embodiments of the invention.

The ablation catheter 24 is then retracted from the PV so that the distal end of the ablation catheter is positioned slightly beyond the distal end of the flexible section 12 at the orifice of the PV. As shown in FIG. 8, depth markings 31 may be provided on the shaft of catheter 24 adjacent catheter handle 27. The depth markings 31 may be used to determine the relative positions of the distal ends of the flexible section 12 and ablation catheter 24. This allows the user to more precisely determine the distance that the catheter tip 26 extends in the PV.

Figure 9:
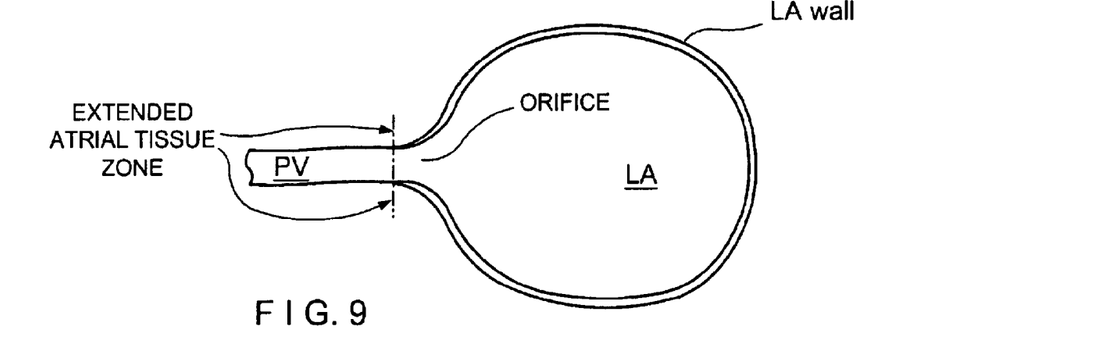
FIG. 9 shows a cross section of the left atrium and pulmonary vein illustrating the extended atrial tissue.

In certain embodiments of the invention, the user may wish to preferably ablate tissue in the extended atrial tissue zone of the PV. As shown in FIG. 9, in the transition region between the left atrium and PV, atrial tissue extends into the PV for about 1–2 cm.

At least two advantages may be obtained by making the ablation in the extended atrial tissue. First, if the ablation is made deeper in the PV and not in the extended atrial tissue, it is believed that in some cases the contraction initiating signal, which originates in the PV, will find a new path, which bypasses the ablated tissue, and resumes the arrhythmia. It is believed that this bypass problem will not occur or will be less frequent when the ablation has been performed in the extended atrial tissue. Second, it is believed that restenosis is more common if the ablation is made more deep in the PV (i.e., in the venous tissue) than if the ablation is made in the extended atrial tissue.

Accordingly, in certain embodiments, once desired catheter tip location has been confirmed, the ablation of tissue may be initiated.

The user supplies a cryogenic fluid to an expansion chamber formed in the cryogenic tip 26 via the cooling fluid lumen 25 to lower the temperature of the cryogenic tip 26 so that an ice ball forms around the tip. Because blood flow from the PV into the LA is substantially impeded by the balloon 18, warming of the cryogenic tip 26 by the flow of blood past the cryogenic tip 26 is minimized and the formation of a large frozen tissue mass or ice ball is facilitated. The ice ball formed may be large enough that it contacts the entire circumference of the inner wall of the PV ablating the tissue and forming a circumferential conduction block between the LA and the site of origination of the improper contraction originating signals.

It may not be desirable to move the cryogenic tip while an ice ball is formed therearound as this ice ball may adhere to tissue and cause damage when moved. If the ice ball formed is not large enough to immediately form a completely circumferential conduction block, the user may ablate a first portion of tissue with a first ice ball and then thaw this first ice ball. The user may reposition the cryogenic tip adjacent to a second portion of tissue to be ablated and form a second ice ball, repeating this process until the entire desired portion of tissue has been ablated thereby forming the circumferential conduction block.

In addition, a user may stun tissue by applying the cryogenic tip 26 thereto at a temperature warmer or for a duration shorter than that required to ablate the tissue. Changes in the path of conduction of the contraction origination signals may then be electrically monitored to further locate the site of origin. A user may also utilize the electrodes at the distal end of the ablation catheter 24 to apply an electric charge to one side of the circumferential conduction block while monitoring the state of the opposite side thereof to determine whether the tissue has been ablated sufficiently to create the desired conduction block.

Figure 10:
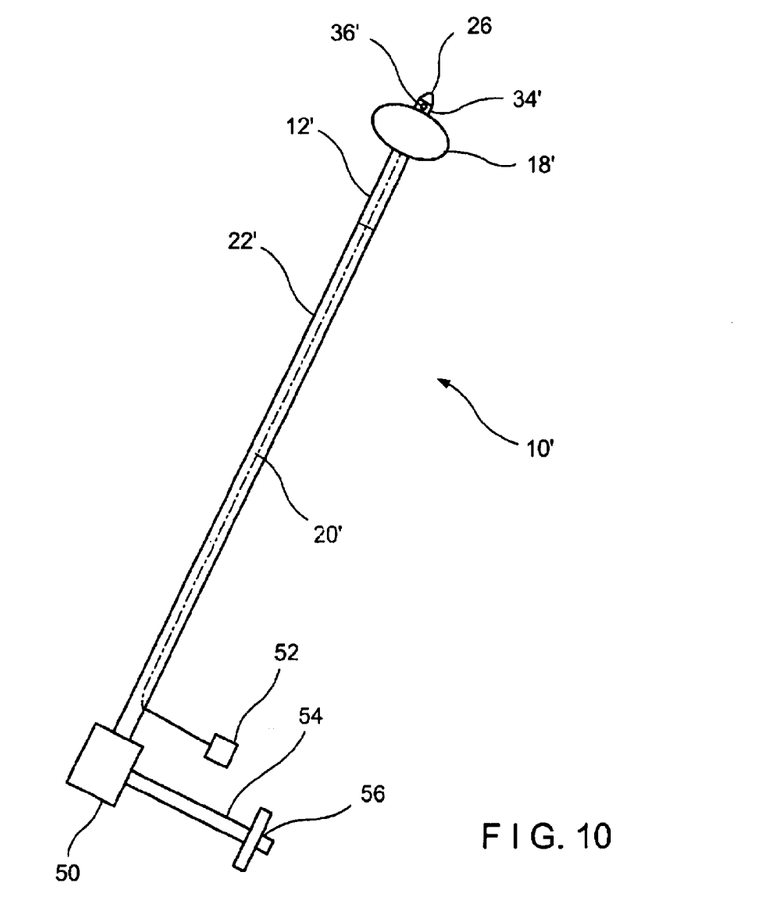
FIG. 10 shows a side view of a device according to an alternate embodiment of the invention.

FIG. 10 shows a device according to an alternate embodiment of the invention wherein a device 10' includes a flexible section 12' formed as a tube extending distally from the distal end of the rigid sheath 22'. The flexible section 12' is coupled to the distal end of the rigid sheath 22' and is preferably not slidable relative thereto. Sections 12' and 22' may be heat fused together. Accordingly, a single sheath may be formed with a flexible section 12' and a rigid section 22.' The inflation lumen 20', which is formed on an outer surface of the sheath extends from an inflation port 52' to balloon 18'. Alternatively, inflation lumen 20' may extend along the interior of the sheath. An ablation catheter 24 as described above in regard to the device 10 is then slidably received through the sheath. In other respects, the device 10' may be constructed in accord with the description of the device 10 above. Ablation catheter 24 may be inserted into the sheath via hemostasis valve 50, which may have a side port 54 and 3-way stopper 56 associated therewith.

Once the device 10' has been inserted into the LA of the patient using the Seldinger technique, the ablation catheter 24 is advanced distally through the rigid section 22' and the flexible section 12' until the cryogenic tip 26 extends distally beyond the distal end of the flexible section 12' and is maneuvered so that the cryogenic tip 26 is within the opening of the one of the PV's from which the contraction origination signals are improperly originating. The balloon 18' is then inflated and the rigid section 22' and the flexible section 12' are then advanced distally along the ablation catheter 24 until the balloon 18' is seated in the orifice at which the PV opens into the LA. As with the device 10, to ensure proper positioning of the cryogenic tip 26, a radiopaque marker 34' is provided adjacent balloon 18'. In addition, radiopaque fluid may be injected into the PV via the opening 36'.

Once the desired position of the ablation catheter 26 has been confirmed, the ablation of tissue may be initiated as described above in regard to the device 10.

Figure 11:
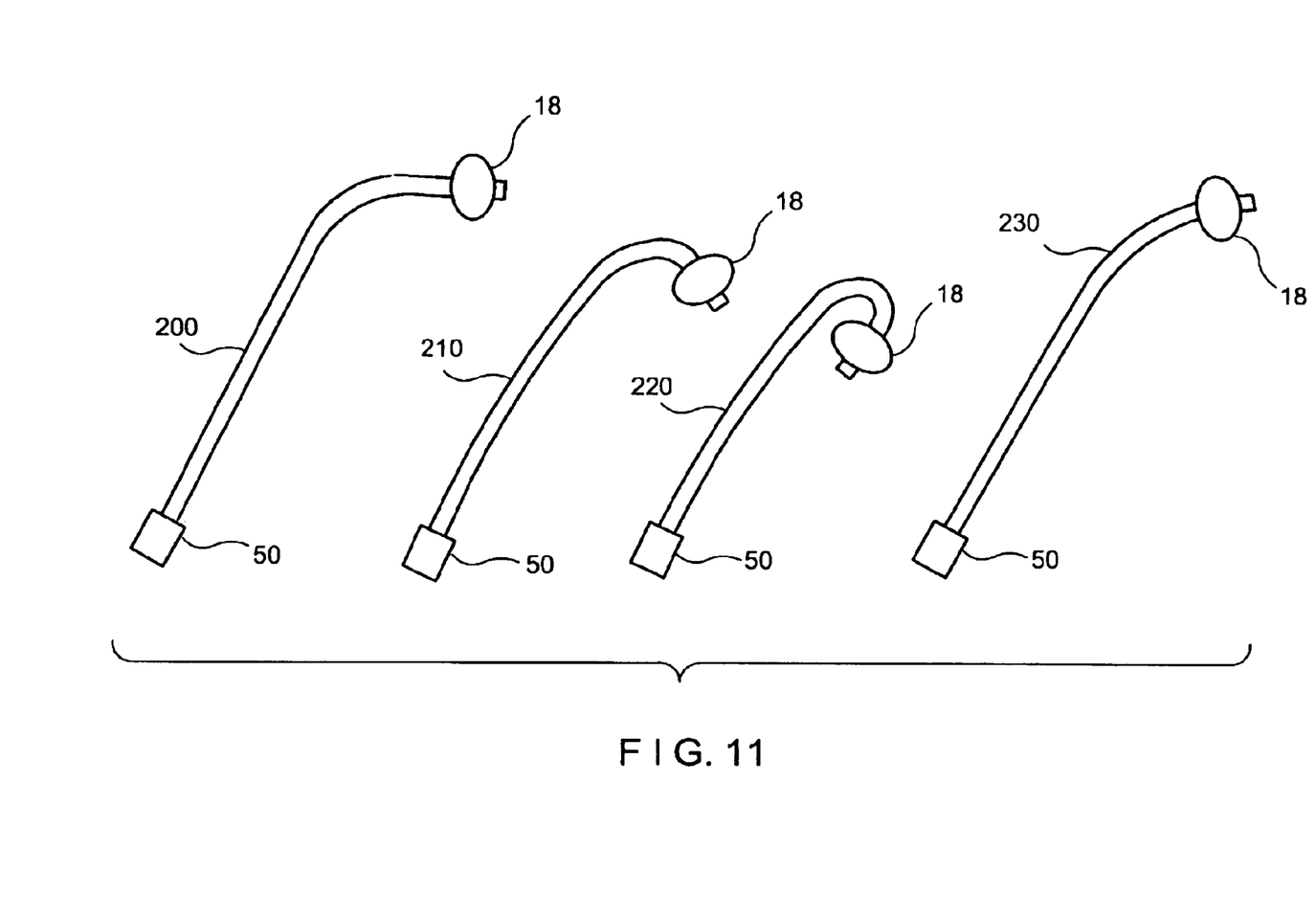
FIG. 11 shows a side view of a collection of pre-shaped rigid sheaths for use with an embodiment of the invention.

Another embodiment of the invention is shown in FIG. 11. In this embodiment, instead of providing a flexible section 12, a plurality of generally rigid sheaths 200, 210, 220 and 230 are provided with various degrees of curvature. While only four sheaths are shown more or less may be provided so as to accommodate various degrees of curvature, e.g., from straight to 180 degrees of curvature. Depending on the patient's anatomy and the particular PV to be treated, the user would select the desired sheath to aid in placement of the catheter and balloon.

In the preceding specification, the present invention has been described with reference to specific exemplary embodiments thereof. It will, however, be evident that various modifications and changes may be made thereto without departing from the broadest spirit and scope of the present invention as set forth in the claims that follow. The specification and drawings are accordingly to be regarded in an illustrative rather than restrictive sense. For example, while the invention has been described for use with PV ablation, the device may be used in other parts of the vasculature.

What is claimed is:

1. A method of ablating tissue within a patient comprising the steps of:
    inserting into a patient's venous system a substantially rigid sheath;
    piercing a desired point of penetration in the patient's interatrial septum to pass the rigid sheath through the interatrial septum into the patient's left atrium;
    maneuvering a flexible section mounted on the rigid sheath into an operative position in which a distal end of the flexible section is located adjacent to a portion of tissue to be ablated, the flexible section including an occluding structure which has a retracted position and extended position;
    extending the occluding structure to the extended position once the flexible section is in the operative position to block blood flow past the occluding structure; and
    passing an ablation catheter through the flexible section so that an ablation tip of the ablation catheter is adjacent to the portion of tissue to be ablated.

2. The method according to claim 1, wherein the portion of tissue to be ablated is located within a pulmonary vein of the patient.

3. The method according to claim 2, wherein the portion of tissue to be ablated is extended atrial tissue.

4. The method according to claim 1, further comprising the step of cooling the ablation tip to cryogenically ablate the portion of tissue to be ablated.

5. The method according to claim 4, wherein an interior of the ablation tip forms an expansion chamber fluidly coupled to a source of high-pressure refrigerant.

6. The method according to claim 1, wherein the flexible section is longitudinally rigid and axially flexible, the flexible section being slidably mounted on the rigid sheath so that, in a first position, a distal end of the flexible section is located proximal to the distal end of the rigid sheath and, in a second position, the distal end of the flexible section is located distal of the distal end of the rigid sheath.

7. The method according to claim 1, wherein the flexible section is longitudinally rigid and axially flexible, a proximal end of the flexible section being mounted to the distal end of the rigid sheath so that a distal end of the flexible section extends distally from the distal end of the rigid sheath.

8. The method according to claim 1, further comprising the step of radially extending the occluding structure to occlude blood flow past the portion of tissue to be ablated.

9. The method according to claim 1, wherein the portion of tissue to be ablated is located within a pulmonary vein of the patient and, wherein the occluding structure includes a balloon coupled to a source of inflation fluid via an inflation lumen extending to an inflation opening which, when the occluding structure is positioned within the body of a patient, remains outside the body.

10. The method according to claim 9, wherein the portion of tissue to be ablated forms a circumferential conduction block to prevent transmission of contraction originating signals to the heart.

11. The method according to claim 1, wherein the rigid sheath includes a radiopaque marker at a distal end thereof to assist in visually positioning the guide sheath.

12. The method according to claim 8, wherein the flexible section includes a dye opening adjacent to the distal end thereof, the dye opening being operatively associated with a dye source that remains outside the body, the method further comprising the step of injecting, after the occluding structure has been radially extended, a radiopaque dye into the pulmonary vein via the dye opening in order to confirm the position of the flexible section or occlusion structure.

13. The method according to claim 8, wherein the flexible section includes a dye opening adjacent to the distal end thereof, the dye opening being operatively associated with a dye source that remains outside the body, the method further comprising the step of injecting, after the occluding structure has been radially extended, a radiopaque dye into the pulmonary vein via the dye opening in order to aid in imaging the pulmonary vein.

14. The method according to claim 1, further comprising the step of moving the ablation tip circumferentially around an inner surface of a pulmonary vein of the patient to create a circumferential conduction block therein to block transmission of contraction originating signals from the pulmonary vein into the patient's heart.

15. The method according to claim 1, wherein the rigid sheath includes a curved section, and when the guide sheath is inserted into the venous system the curved section extends from the inferior vena cava into the right atrium such that the distal end of the rigid sheath is directed toward an approximate location of a desired point of penetration in the patient's interatrial septum.

16. A method of treating arrhythmias originating in a pulmonary vein of a patient, comprising:
    inserting a sheath having a proximal section and a distal section into a patient's left atrium, wherein the distal section is more flexible than the proximal section;
    passing an ablation catheter through the sheath and into a desired pulmonary vein;
    inflating an occluding structure mounted on the distal section of the sheath, outside of the pulmonary vein to block the flow of blood from the pulmonary vein into the left atrium;
    maneuvering the sheath along the ablation catheter such that the occluding structure seats against an orifice of the desired pulmonary vein;
    maneuvering a tip of the ablation catheter to a portion of tissue desired to be treated, whereby the known position of the occluding structure is used to facilitate this process; and
    treating the desired tissue with the ablation catheter.

17. The method according to claim 16, wherein the desired tissue is extended atrial tissue.

18. A system for ablating tissue comprising:
    a substantially rigid guide sheath having a curved section dimensioned so that, when the guide sheath extends from a right atrium of a patient through an interatrial septum to a left atrium, a distal end of the guide sheath may be rotated to face an opening into a pulmonary vein laterally spaced from an axis of a portion of the rigid sheath extending through the interatrial septum;
    a flexible section mounted on the rigid sheath, the flexible section being substantially longitudinally rigid and axially flexible, a distal end of the flexible section including an occluding structure mounted thereto and having an extended configuration for blocking a flow of blood therepast and a retracted configuration; and an ablation catheter including an ablation tip at a distal end thereof, the ablation catheter being slidably mounted within the rigid sheath and flexible section so that the ablation tip may be moved from a first position in which the ablation tip is received within the rigid sheath to a second position in which the ablation tip is extended therefrom.

19. The system according to claim 18, wherein an interior of the ablation tip forms an expansion chamber coupled to a source of high-pressure refrigerant.

20. The system according to claim 18, wherein the flexible section is slidably received around an outer surface of the rigid sheath so that the distal end of the flexible section may be moved between a first position in which the distal end of the flexible section is located proximally of the distal end of the rigid sheath and a second position in which the distal end of the flexible section is located distally of the distal end of the rigid sheath.

21. The system according to claim 18, wherein a proximal end of the flexible section is coupled to the distal end of the rigid sheath.

22. The system according to claim 18, wherein the occluding structure includes a balloon coupled to a source of inflation fluid.

23. The system according to claim 18, wherein the ablation catheter is cryogenic.

24. A method of ablating tissue within a patient comprising the steps of:

inserting into a patient's left atrium a substantially rigid sheath;

maneuvering a flexible section mounted on the rigid sheath into an operative position in which a distal end of the flexible section is located adjacent to a portion of tissue to be ablated in a pulmonary vein, the flexible section including an occluding structure which has a retracted position and an extended position;

passing an ablation catheter through the flexible section so that an ablation tip of the ablation catheter is adjacent to the portion of tissue to be ablated; and extending the occluding structure to the extended position once the flexible section is in the operative position to block blood flow through the pulmonary vein past the portion of tissue to be ablated.

25. The method according to claim 24, wherein the flexible section is longitudinally rigid and axially flexible, the flexible section being mounted on the rigid sheath so that, in a first position, a distal end of the flexible section is located proximal to the distal end of the rigid sheath and, in a second position, the distal end of the flexible section is located distal of the distal end of the rigid sheath.

26. The method according to claim 24, wherein the flexible section includes a dye opening adjacent to the distal end thereof, the dye opening being operatively associated with a dye source that remains outside the body, the method further comprising the step of injecting, after the occluding structure has been radially extended, a radiopaque dye into the pulmonary vein via the dye opening in order to confirm the position of the flexible section or occlusion structure.

27. A system for ablating tissue within a pulmonary vein comprising:

a substantially rigid sheath having a curved section dimensioned so that, when the guide sheath extends from a right atrium of a patient through an interatrial septum to a left atrium, a distal end of the guide sheath may be rotated to face an opening into a pulmonary vein laterally spaced from an axis of a portion of the rigid sheath extending through the interatrial septum;

a flexible section mounted on the guide sheath, the flexible section being substantially longitudinally rigid and axially flexible, a distal end of the flexible section including an occluding structure mounted thereto and having an extended configuration for blocking a flow of blood therepast and a retracted configuration; and an ablation catheter including an ablation tip at a distal end thereof, the ablation catheter being slidably mounted within the rigid sheath and flexible section so that the ablation tip may be moved from a first position in which the ablation tip is received within the rigid sheath to a second position in which the ablation tip is extended distally from a distal end thereof.

* * * * *